United States Patent [19]

Matsuzaki et al.

[11] Patent Number: 5,495,764
[45] Date of Patent: Mar. 5, 1996

[54] VIBRATION MEASUREMENT SYSTEM FOR A ROLLING BEARING

[75] Inventors: Hiroyuki Matsuzaki; Hisakazu Tadokoro, both of Kanagawa, Japan

[73] Assignee: NSK Ltd., Tokyo, Japan

[21] Appl. No.: 417,962

[22] Filed: Apr. 6, 1995

[30] Foreign Application Priority Data

Apr. 6, 1994 [JP] Japan .................................. 6-092999

[51] Int. Cl.⁶ .................................................. G01M 13/04
[52] U.S. Cl. .................................................. 73/593
[58] Field of Search ........................... 73/593, 660, 587, 73/665; 340/682

[56] References Cited

U.S. PATENT DOCUMENTS

| 3,596,502 | 8/1971 | Bayre et al. | 73/593 |
| 4,991,442 | 2/1991 | Matsumoto | 73/660 |
| 5,033,317 | 7/1991 | Van Haag | 73/862.54 |
| 5,263,372 | 11/1993 | Matsuzaki et al. | 73/593 |
| 5,423,218 | 6/1995 | Matsuzaki | 73/593 |

FOREIGN PATENT DOCUMENTS

| 4219318 | 12/1992 | Germany | 73/593 |
| 1448233 | 12/1988 | U.S.S.R. | 73/593 |
| 1237721 | 6/1971 | United Kingdom . | |

*Primary Examiner*—Hezron E. Williams
*Assistant Examiner*—Rose M. Finley
*Attorney, Agent, or Firm*—Sughrue, Mion, Zinn, Macpeak & Seas

[57] ABSTRACT

A vibration measurement system 1 comprises a shrink-type chuck 5, a spindle 14, and a servo motor 16 as mechanical elements, and has a vibration pickup 41 attached to the outer peripheral surface of a jaw 5a holding an outer ring 4 of a roller bearing 2. A ring groove 5b is formed on the inner face of the jaw 5a holding the bearing 2, and a shell 18 with oil pressure as back pressure is fitted into the ring groove 5b. When vibration is measured, the oil pressure of the shell 18 is raised to bring bearing clearance to zero, thereby preventing so-called roller drop from causing impulsive vibration.

4 Claims, 6 Drawing Sheets

CHUCK PRESSURE

VIBRATION MEASUREMENT SYSTEM FOR A ROLLING BEARING

BACKGROUND OF THE INVENTION

1. Field of the Invention

The present invention relates to a vibration measurement system for a rolling bearing which measure vibration, that is, displacement, velocity, acceleration change and elastic wave of a rolling bearing.

2. Related Art

A conventional known vibration measurement system of a rolling bearing comprises drive device for rotating an outer or inner ring, a vibration pickup for detecting vibration or an elastic wave (hereinafter, the "vibration" contains elastic wave) of the outer or inner ring, and a frequency converter for analyzing a signal detected by the vibration pickup.

The vibration measurement system analyzes detected vibration, that is, displacement, velocity, acceleration change and elastic wave (AE signal) and, for example, checks the bearing ring which is an inner or outer ring of a rolling bearing or the rolling face of a plurality of rolling elements, i.e., roller or ball, for flaw, surface roughness, waviness, defective form, foreign material, etc., and monitors an abnormal condition occurring on the bearing in an endurance test, etc.

For a bearing having no contact angle, such as a cylindrical roller bearing, needle bearing, or water pump bearing of ball or roller type, the conventional vibration measurement system imposes a radial load or a moment load on an outer ring and locally removes clearance between a rolling element such as a roller and a bearing ring, then in this state, drives the bearing for executing vibration evaluation of the bearing unit. For a bearing having a contact angle, such as a ball bearing, the vibration measurement system drives the bearing for executing vibration evaluation of the bearing unit in a state in which an axial load is imposed in accordance with the dimensions of the bearing.

However, the conventional rolling bearing vibration measurement system suffers from the following problems: Although a load zone with no clearance between the rolling element and the bearing ring can be formed by imposing a radial or moment load locally on the outer ring in a bearing such as a roller bearing having no contact angle, a non-load zone in which clearance occurs between the rolling element and the bearing ring is formed in other portions. If the bearing is driven in the state, a phenomenon of so-called roller drop occurs in which the rolling element collides with the bearing ring on the boundary where the rolling element moves from the load zone to the non-load zone, causing impulsive vibration to occur. FIG. 8 is a graph of measured vibration signal. A large peak signal i is caused by impulsive vibration and is mixed with evaluation information such as a rolling face flaw, thus making bearing vibration evaluation difficult to execute. Even if shock is comparatively light, roller slide, etc., makes correct evaluation difficult to execute.

Further, for evaluation over a full periphery of a fixed ring, the conventional vibration measurement system may rotate the fixed ring little by little and move the load zone, but the total measurement time is prolonged and the vibration measurement system needs to perform complicated control because of repeating the steps of rotating the fixed ring and then executing measurement.

On the other hand, to fit a bearing such as a ball bearing having a contact angle to an actually used machine, a close fit is often used for creep prevention during operation. In such a state, elastic deformation to the inner or outer ring side is made, thus the contact angle decreases and the running position of a rolling element such as a steel ball is shifted to the groove center of a bearing ring. The difference between the contact angle during vibration evaluation of the bearing unit and that in practical use is often at stake. Up to now, effective countermeasures have not been provided.

To solve the problems, extremely accurate working is required for finishing the dimensions of the fit part of a rolling bearing to be measured (the outer diameter of a mounting shaft into which an inner ring, etc., is fitted and the inner diameter of a housing to which an outer ring is attached) to the dimensions to allow the bearing clearance when the rolling bearing is fitted to become a predetermined value (zero when the rolling bearing has no contact angle or a clearance distance to allow the contact angle to become a preset angle with a predetermined axial load imposed when the rolling bearing has a contact angle). Although the design dimensions are the same, the dimensions vary from one rolling bearing to another. Each time the measurement object changes, the fit part must be matched with it. Further, if an interference is made too large, deformation affecting the bearing ring and rolling element forms, etc., occurs and correct evaluation may be unable to be executed.

SUMMARY OF THE INVENTION

The present invention was made in view of the foregoing problems accompanying the conventional vibration measurement system. Therefore, an object of the invention is to provide a vibration measurement system capable of accurately measuring vibration of a rolling bearing.

The above and other objects can be achieved by a provision of a vibration measurement system of a rolling bearing which, according to the present invention, includes a hold member into which a rolling bearing having at least one bearing ring and a plurality of rolling elements is fitted, a drive member for driving the rolling bearing fitted into the hold member and causing the rolling elements to make rolling motion relative to the bearing ring, and a vibration detecting member for detecting a vibration of the rolling bearing. The vibration measurement system of the invention improves by a provision of a member for elastically deforming uniformly radially the hold member into which the rolling bearing is fitted, clearance detection member for detecting a state amount indicating a fit state between the rolling bearing and the hold member, and deformation control member for enabling the deformation member to elastically deforming the hold member until a bearing clearance distance corresponding to the state amount indicating the fit state detected by the clearance detection member reaches a predetermined value.

The vibration measurement system of a rolling bearing of the invention drives a rolling bearing with the rolling bearing fitted into the hold member and causes the rolling elements to make rolling motion relative to the bearing ring by the drive means, and detects vibration of the rolling bearing by the vibration detection means. At the time, the vibration measurement system elastically deforms radially uniformly the hold member into which the rolling bearing is fitted by the deformation member, detects a state amount indicating the fit state between the rolling bearing and the hold member by the clearance detection member, and enables the deformation member to elastically deforming the hold member by the deformation control member until the bearing clearance distance corresponding to the state amount indicating the detected fit state reaches a predetermined value.

Therefore, elastic deformation can be given to the bearing ring radially uniformly without putting out of shape the bearing ring deformed with elastic deformation of the hold member by the deformation member. For the outer ring, the bearing ring shrinks; for the inner ring, it expands. Thus, the bearing clearance of the rolling bearing built in the vibration measurement system is adjusted to a predetermined distance.

BRIEF DESCRIPTION OF THE DRAWINGS

FIG. 2 is a sectional view showing the structure of an outer ring constraint part 5a;

DESCRIPTION OF THE PREFERRED EMBODIMENTS

Figure 1:
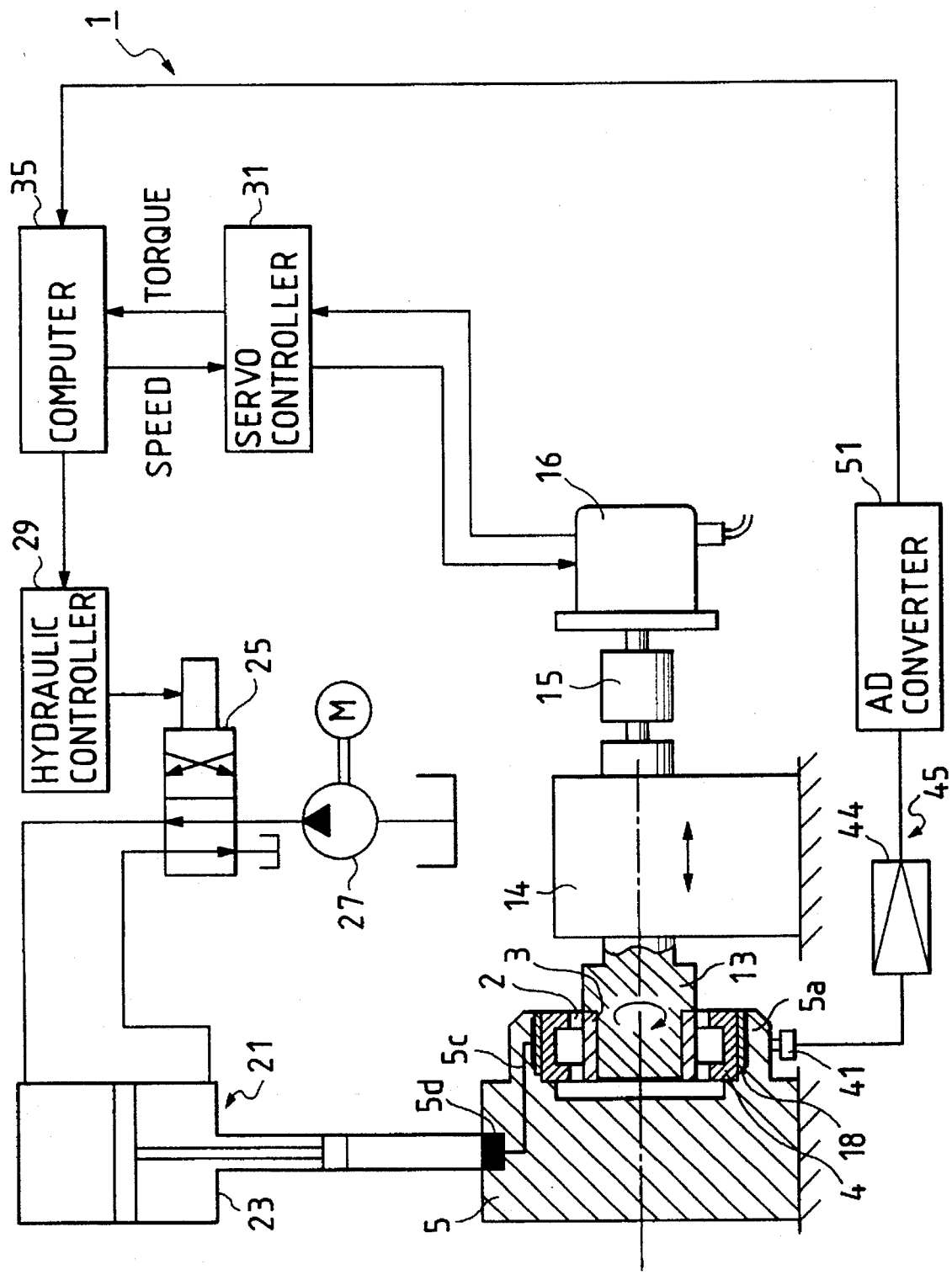
FIG. 1 is a block diagram schematically showing a vibration measurement system of a rolling bearing according to a first embodiment of the invention.

Referring now to the accompanying drawings, preferred embodiments of the invention will be described in detail.
First embodiment FIG. 1 is a block diagram to schematically show a vibration measurement system of a rolling bearing according to a first embodiment of the invention. The vibration measurement system 1 of the first embodiment includes a known shrinkage-type chuck 5 as a hold member, a spindle 14, and a servo motor 16 as main mechanical elements. The chuck 5 holds a roller bearing 2 to be measured, and an arbor 13 attached to the tip of the spindle 14 is fitted to an inner ring 3 of the roller bearing 2. The spindle 14 is connected via a coupling 15 to a rotation shaft of the servo motor 16. The spindle 14 and the servo motor 16 can move axially by a slide mechanism with a ball screw, etc., (not shown).

Figure 2:
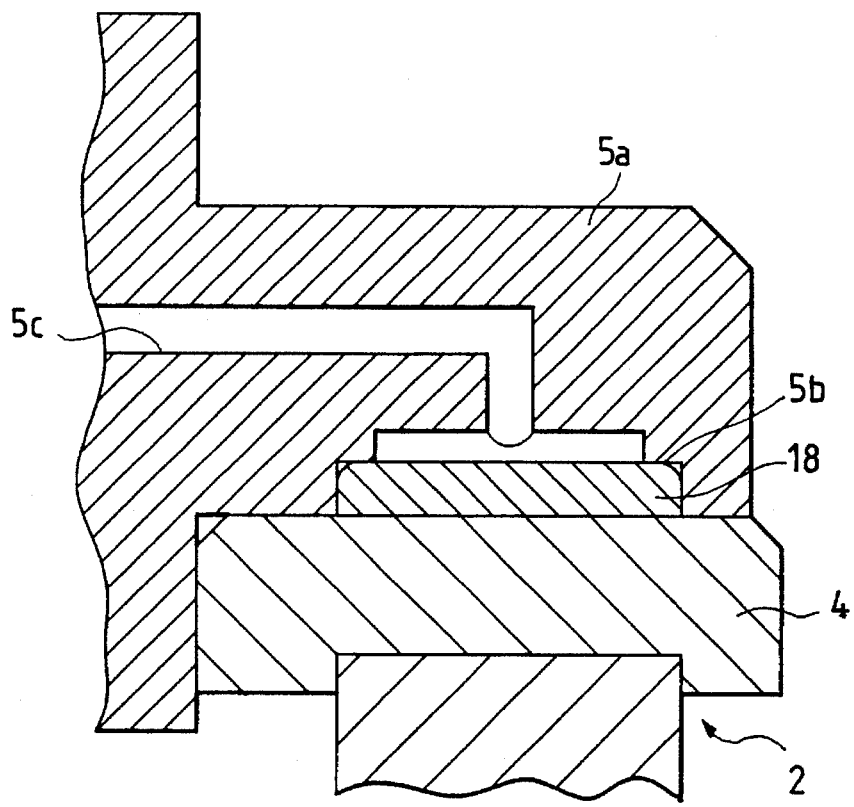

A ring groove 5b is formed on the inner face of an outer ring constraint part 5a for holding the roller bearing 2 of the chuck 5. FIG. 2 is a sectional view showing the structure of the outer ring constraint part 5a. A circular ring shell 18 which is thin is fitted to the ring groove 5b. The shell 18 is in contact with an outer ring 4 of the roller bearing 2 and is shrank in a radial direction upon reception of back pressure from a hydraulic system 21 described below. A communication passage 5c connecting the ring groove 5b and a port 5d above it is formed in the chuck 5, and is held in an oil-tight condition. The hydraulic system 21 comprises a booster 23 made of a hydraulic cylinder, a servo valve 25, a hydraulic pump 27, and a hydraulic controller 29, and controls oil pressure communicated with the upper port 5d of the chuck 5.

The servo motor 16 is an AC servo motor controlled by a servo controller 31 and has the rotation shaft to which a rotary encoder (not shown) is attached. The servo controller 31 receives a given velocity command signal from a computer 35 and performs position feedback control and velocity feedback control of the servo motor 16 in response to a pulse signal from the rotary encoder.

A vibration pickup 41 as vibration detection member is attached to the outer face of the outer ring constraint part 5a of the chuck 5. It detects vibration propagating in the radial direction or axial direction from the outer ring 4 and outputs a detection signal to a signal measurement section 45 consisting of an amplification section 44 and an A/D converter 51. The amplification section 44 comprises an amplifier and a low-pass filter; a signal amplified by the amplification section 44 is sent to the A/D converter 51, which then converts the signal into a digital signal. The computer 35 makes a frequency analysis of vibration based on the digital signal received from the A/D converter 51.

Next, a measurement procedure of the rolling bearing vibration measurement system of the embodiment will be discussed. Before measurement is started, the spindle 14 is saved by the slide mechanism, the roller bearing 2 to be measured is inserted into the inside of the outer ring constraint part 5a of the chuck 5, and the spindle 14 is moved closer to the chuck 5 for fitting the arbor 13 mounted on the tip of the spindle 14 into the inner ring 3 of the roller bearing 2.

Further, to bring the bearing clearance of the roller bearing 2 to zero, the hydraulic system 21 is operated to shrink the shell 18. The shrinkage amount of the shell 18 is determined by the clearance between the shell 18 and the outer ring 4 of the roller bearing 2 and the bearing clearance of the bearing 2. The pressure required to shrink the shell 18 is derived from the relationship of the radial displacement amount of a cylinder to external pressure (or internal pressure), for example, by FEM (finite element method) based on elastic deformation theory of cylinder (for example, see Kikai Kogaku Binran (mechanical engineering handbook), Part 4, Zairyo Rikigaku (mechanics of materials), p98-). Since the bearing clearance has a given distribution and the roller dimensions vary from one to another about one bearing, the shell shrinkage condition under which the bearing clearance reaches zero varies depending on the bearing. Therefore, the bearing clearance is brought to zero and the chuck pressure (back pressure of the shell 18) needs to be controlled so that excessive face pressure does not occur between the roller and bearing ring surface.

Figure 3:
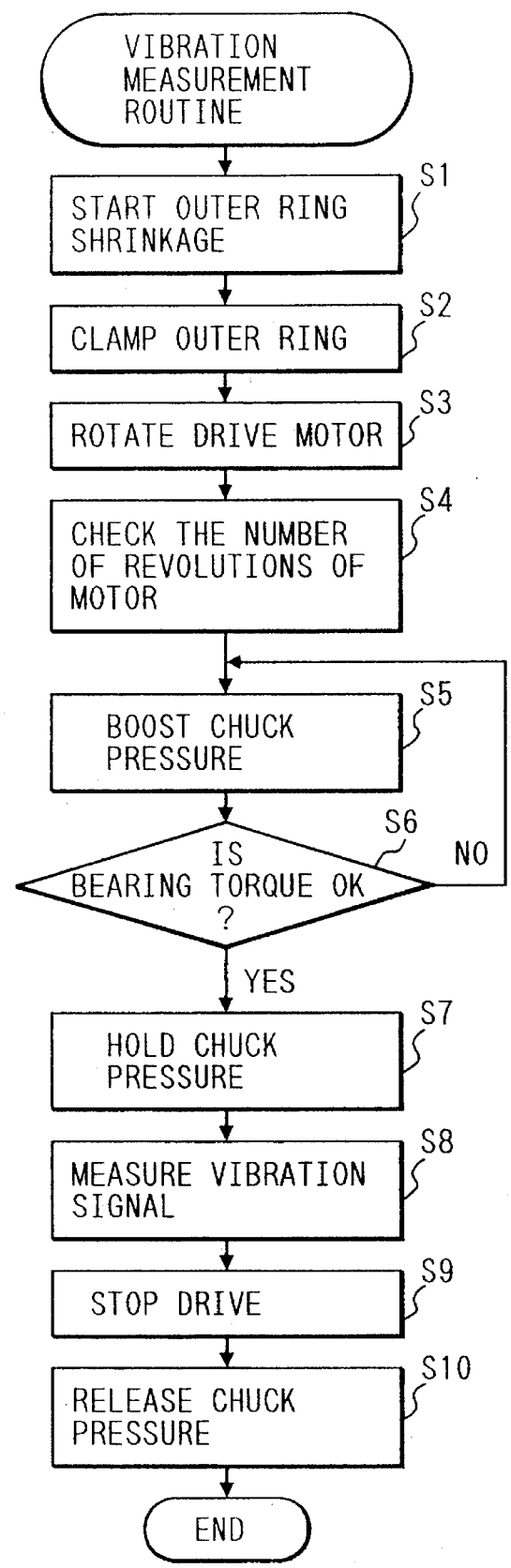
FIG. 3 is a flowchart showing a vibration measurement routine for controlling chuck pressure.

FIG. 3 is a flowchart showing a vibration measurement routine for controlling the chuck pressure. The vibration measurement routine is executed by the computer 35. First, the computer 35 outputs outer ring shrinkage start signal to the hydraulic system 21 at step S1 and lightly clamps the outer ring 4 at step S2. With the outer ring 4 held to prevent sliding, the servo motor 16 is started to given rotational velocity at steps S3 and S4. Next, the computer 35 outputs a pressure boost signal to the hydraulic system 21 for gradually boosting the chuck pressure at steps S5–S6. Then, the bearing torque changes.

Figure 4:
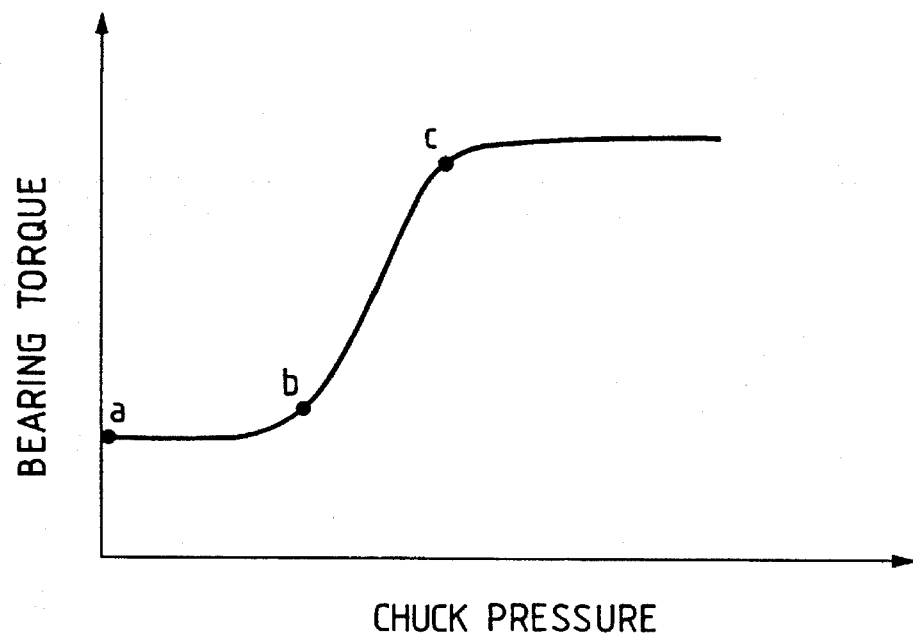
FIG. 4 is a graph of bearing torque change in response to chuck pressure.

FIG. 4 is a graph of bearing torque change in response to the chuck pressure. When the chuck pressure exists between a and b, the roller bearing 2 is in a clearance condition and the bearing torque is mainly viscous resistance of grease. Further, when the chuck pressure raises and a contact between the roller and the bearing ring is started at point b, the torque rapidly increases. When point c is exceeded, increase in the bearing torque rapidly lessens. Therefore, it can be assumed that almost all rollers come in contact with the bearing ring at the inflection point c. The chuck pressure is held at the inflection point c at step S7, vibration from the roller bearing 2 is detected by the vibration pickup 41, and known signal processing is performed for determination at step S8. At steps S5 and S6, the bearing torque can be found by monitoring the armature current of the servo motor 16. That is, since the electric current flowing in the armatures corresponds to the torque of the load as known, a factor of proportionality is first determined for calculating the value of load torque from the current of armature of the servo motor 16, and the factor of proportionality is stored in a memory of the computer 35. Then the computer 35 multiplies the current of armature input from the servo controller 31 by the factor of proportionality stored in the memory so that the load torque is calculated. The computer 35 stores the current of armature which is continuously input thereto at every predetermined sampling cycle which is appropriately determined to be sufficiently smaller than the speed of pressure increase of the chuck and necessarily sufficient for the calculation discussed above and the calculation of the torque detection. The computer 35 repeats the calculation in every sampling cycle. On the other hand, the judgement of whether the point c is exceeded is carried out, for example, by judging whether a predetermined torque value, i.e., a torque value corresponding to a point between the points b and c shown in FIG. 4 and as close to the point c, is exceeded, or by observing a variation of the difference from the formerly calculated value. At the termination of the measurement, driving the servo motor 16 is stopped at step S9, the chuck pressure is released at step S10, and the routine is terminated.

In the first embodiment, the state amount indicating the fit state of the rolling bearing is the bearing torque and a predetermined value of the bearing clearance amount in the fit state is zero.

The vibration measurement system 1 of the embodiment can prevent so-called roller drop in which the roller collides with the bearing ring, and provide correct vibration evaluation.

Second embodiment

Figure 5:
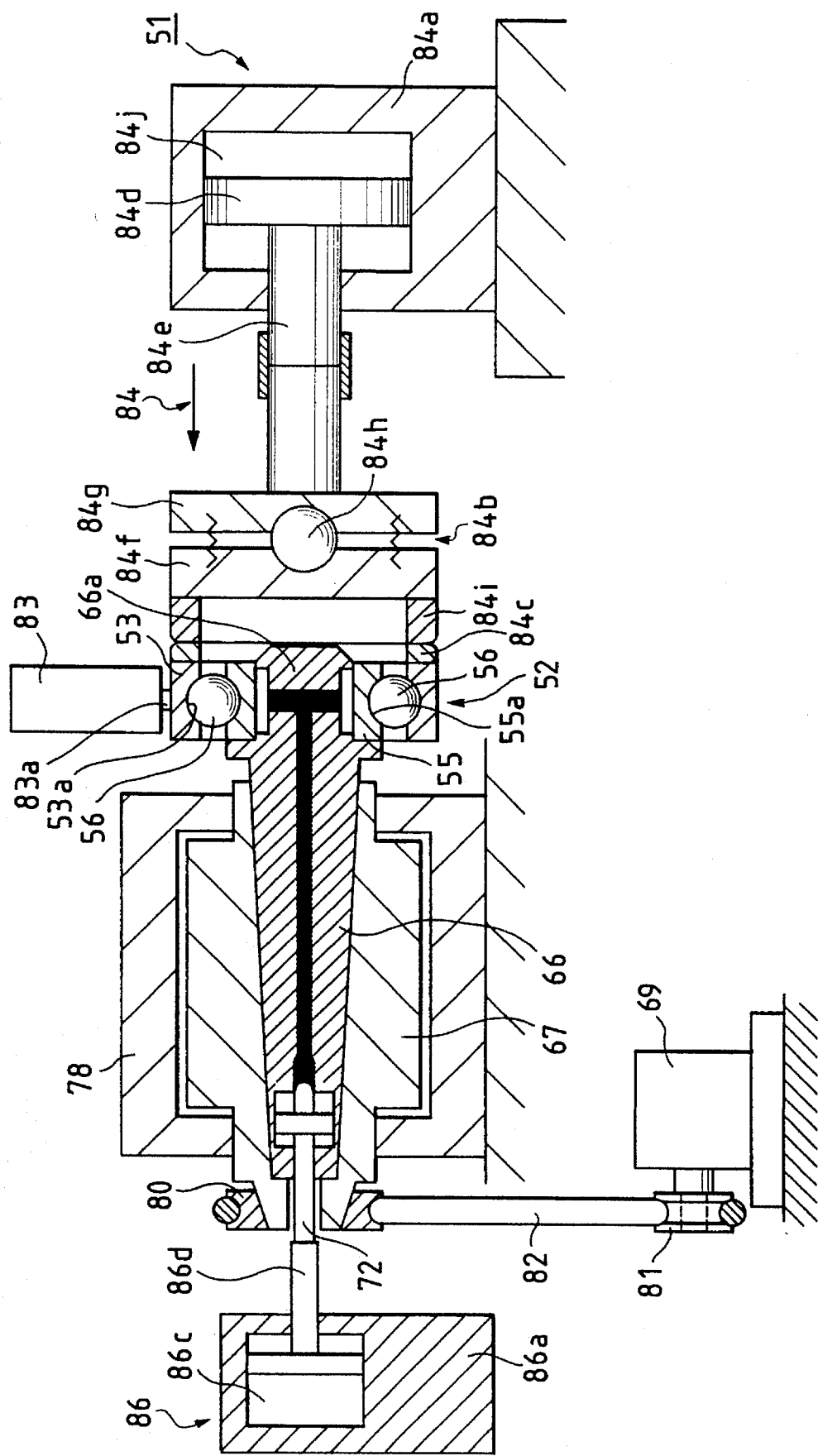
FIG. 5 is a sectional view showing the mechanical structure of a vibration measurement system according to a second embodiment.
Figure 6:
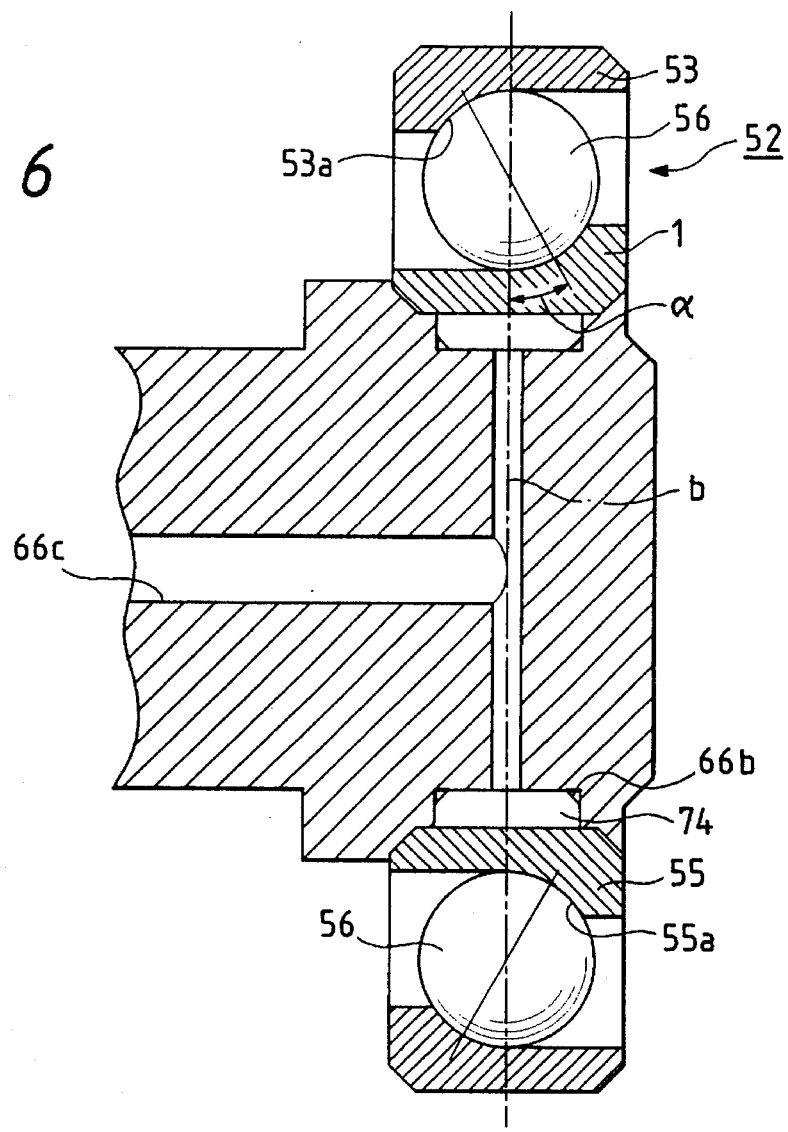
FIG. 6 is a sectional view showing the structure of a ball bearing 52.
Figure 8:
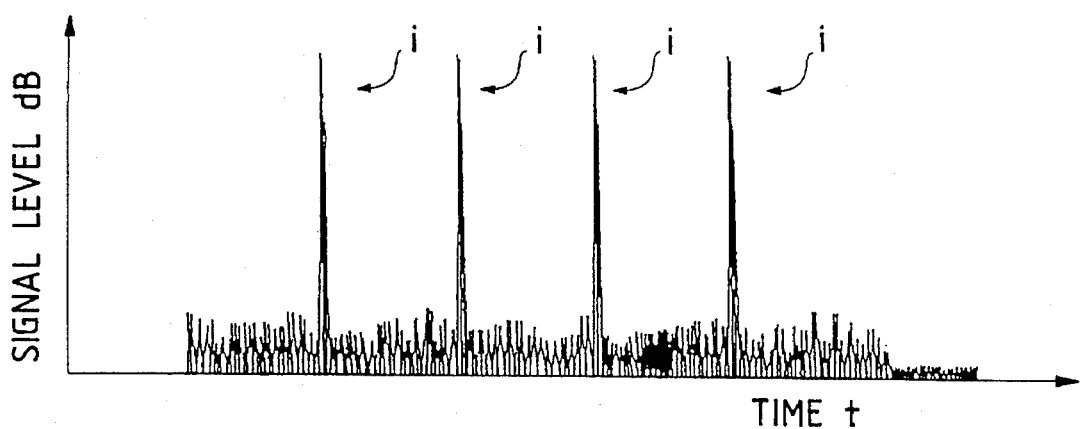
FIG. 8 is a graph of vibration signal measured in a state in which bearing clearance exists.

Next, a vibration measurement system of a rolling bearing according to a second embodiment of the invention will be discussed. FIG. 5 is a sectional view showing the mechanical structure of the vibration measurement system of the second embodiment. The vibration measurement system 51 of the second embodiment measures vibration of ball bearings rather than roller bearings whose vibration is measured in the first embodiment. FIG. 6 is a sectional view showing the structure of a ball bearing 52. The ball bearing 52 is one type of rolling bearing having a contact angle $\alpha$ and has an outer ring 53, an inner ring 55, and a plurality of balls 56, rolling elements between a track 53a of the outer ring 53 and a track 55a of the inner ring 55. The vibration measurement system 51 comprises a spindle 67, an outer ring press device 84, a booster 86, and a servo motor 69 as mechanical elements.

A taper hole is formed at the center of one end surface of the spindle 67 and an arbor 66 is fitted into the hole. The arbor 66 as a hold member forming a known expand-type chuck is fitted into the inner ring 55 of the ball bearing 52. As a bearing structure 78 for rotatably supporting the spindle 67, any structure may be used if it does not generate vibration with rotation of the spindle 67, such as a static pressure gas bearing, a magnetic bearing, or a superconductive bearing.

A ring groove 66b is formed on the side of a tip 66a of the arbor 66 in contact with the inner ring 55 of the ball bearing 52, and a shell 74 is fitted to the outside of the ring groove 66b. A communication passage 66c of oil pressure for deforming the shell 74 is formed inside the ring groove 66b, and a piston 72 is disposed at the rear of the communication passage 66c. The oil pressure in the communication passage 66c is adjusted by pressing the piston 72. The booster 86 comprising a hydraulic cylinder 86a is disposed at the rear of the piston 72. The hydraulic cylinder 86a comprises a piston 86d provided in a cylinder chamber 86c, and receives a supply of oil pressure from an oil pressure generator (not shown) similar to that in FIG. 1. Therefore, when the piston 72 is pushed by the booster 86, the shell 74 on the side of the tip 66a of the arbor 66 into which the ball bearing 52 is fitted expands in a radial direction. Upon reception of expansion pressure of the shell 74, the inner ring 55 of the ball bearing 52 also expands in the radial direction, decreasing the contact angle $\alpha$.

The spindle 67 can be rotated by the servo motor 69 and a belt 82 is placed on a driven pulley 80 fixed to the rear of the spindle 67 and a driving pulley 81 fixed to an output shaft of the servo motor 69. When the servo motor 69 is energized, the spindle rotates at a constant velocity of about 1800 rpm, for example.

The outer ring press device 84 is fixed facing the end surface of the outer ring 53 of the ball bearing 52 supported by the arbor 66. It has a pressurization cylinder 84a, a swing joint 84b, and a press ring 84c. The base end of a rod 84e is fixed to a pressurization piston 84d fitted into the pressurization cylinder 84a, and the swing joint 84b is coupled to the tip of the rod 84e. The swing joint 84b enables swing displacement of two plate pieces 84f and 84g by sandwiching a sphere 84h between the plate pieces 84f and 84g.

The press ring 84c is supported via a buffer 84i on the side of one plate piece 84f facing the ball bearing 52. As a pressure fluid is fed into the cylinder chamber 84j of the pressurization cylinder 84a, the press ring 84c is pressed against the end surface of the outer ring 53 of the ball bearing 52, axially pressing the outer ring 53. If the inner ring 55 rotates when the servo motor 69 is energized, the pressing prevents the outer ring 53 from rotating and applies predetermined axial pressure to the ball bearing 52.

During the pressing, the swing joint 84b has a role of pressing the press ring 84c against the end surface of the outer ring 53 over the full periphery by a uniform force. The buffer 84i prevents vibration occurring at the pressurization cylinder 84a or the swing joint 84b from being propagated to the outer ring 53. As the means for axially pressing the press ring 84c, another mechanism such as a solenoid can also be used in place of the pressurization cylinder.

A probe 83a of the vibration pickup 83 abuts the outer peripheral surface of the outer ring 53. The vibration pickup 83 measures vibration propagating in the radial direction of the outer ring 53. Only the mechanical elements of the vibration measurement system 51 are shown in FIG. 5; a signal measurement section for measuring an output signal from the vibration pickup 83, a hydraulic system for driving the hydraulic cylinder 86a and the pressurization cylinder 84a, and a servo controller for driving the servo motor 69 are identical with or similar to those discussed in the first embodiment and therefore will not be discussed again.

Figure 7:
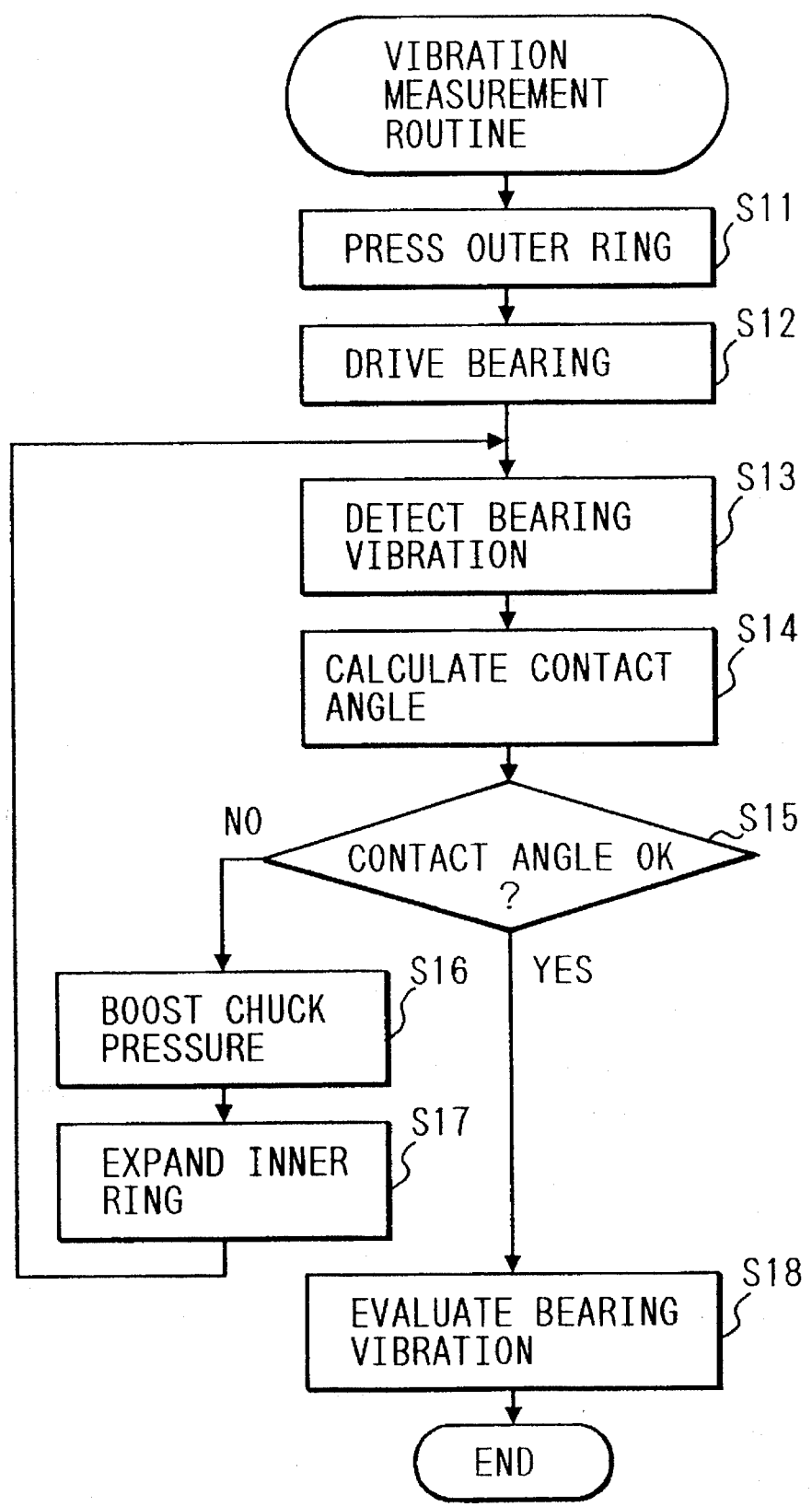
FIG. 7 is a flowchart showing a vibration measurement routine according to the second embodiment.

Next, the measurement operation of the vibration measurement system 51 will be discussed. FIG. 7 is a flowchart showing a vibration measurement routine according to the second embodiment. The vibration measurement routine is executed by a computer (not shown) similar to that of the first embodiment.

First, the outer ring press device 84 is driven for axially pressurizing the outer ring 53 of the ball bearing 52 via the buffer 84i and the vibration-isolated press ring 84c at step S11. Then, the servo motor 69 is driven for rotating the inner ring 55 of the ball bearing 52 at step S12. Vibration in the radial direction of the outer ring 53 occurring with the rotation of the ball bearing 52 is sensed by the vibration pickup 83 at step S13. Contact angle α is calculated based on the sensed vibration signal at step S14. The contact angle α is calculated by a known calculation method described in Japanese Patent Laid-Open No.Hei 4-364408. That is, the contact angle α is calculated according to Expression 1:

$$\alpha = \cos^{-1}[dm \cdot \{1-(2fc/fr)\}/Da]$$

where Da is the outer diameter of the ball 56 and dm is the trajectory of revolution of the ball 56. Therefore, the values of Da and dm are predetermined dimensions. fc and fr are the revolution frequency of the ball 56 and the rotation frequency of the inner ring 53 respectively. They are calculated by the computer (not shown) for the following reason:

The reason why the revolution and rotation frequencies of the ball 56 and the inner ring 55 are found is as follows: The members making up the ball bearing 52 are finished extremely accurately, but the surface form and dimensions contain a minute error. For example, the track of the outer ring 53 is very slightly off-centered with respect to the rotation center. This eccentricity causes the rotation frequency component to vibrate. The rotation frequency of the inner ring 55 can be known by measuring vibration in the radial direction of the outer ring 53. The balls 56 built in the ball bearing 52 should be the same in outer diameter, but it is difficult to complete the balls of the same diameter because of a manufacturing error. As the balls 56 subtly different in outer diameter revolve, the outer ring 53 vibrates in the radial direction. The frequency of the vibration contains the revolution frequency component of the ball 52. Therefore, if the vibration frequency is found, the revolution frequency of the ball 56 can be found.

That is, as disclosed in Unexamined Japanese Patent Application No. Hei. 4-364408, when the arbor rotating constantly is inserted to the inner diameter of the inner ring of the bearing, the inner ring starts to rotate together with the arbor. In accordance with the rotation of the inner ring, the rolling elements which is arranged in the circumferential direction at an equal interval by the hold member starts the revolution in the rotational direction of the inner ring. At this time, while the outer ring is still unrotated, the vibration pickup comes into contact with the outer circumferential surface of the outer ring so that the vibration of the bearing is converted into electric signals. The vibration detected by the vibration pickup includes mixture of vibrations in the radial direction, angled direction and axial direction based upon the revolution of the plurality of rolling elements and according to the swell of the ring surface of the outer ring. Since these frequency of vibrations coincide with the revolution cycle of the rolling elements and a frequency which is a multiple of integer of the revolution frequency fc of the rolling elements, the revolution frequency fc can be calculated from the vibration frequency. Accordingly, the revolution frequency fc can be calculated if one of the vibration frequencies in the three directions of the outer or inner ring is detected. Further, since the rotation frequency fr (rev/sec: constant) is known from the rotational number of the inner ring, the relationship between the revolution frequency fc and the contact angle α are calculated by the expression 1 using known factors dm and Da. In other words, the revolution frequency fc is calculated by one of the vibration signals in the three directions detected by the vibration pickup, and the contact angle α is determined by the expression 1 when fc/fr is applied.

The pressure deforming the shell 74 is controlled by the booster 86 pressing the piston 72 until the calculated contact angle α becomes a predetermined contact angle αA at steps S15 to S17. When α becomes αA, the pressure is held for maintaining expansion of the inner ring 55. With the inner ring 55 expanded, radial or axial vibration of the outer ring 55 of the ball bearing 52 is detected, and flaws and defects of the form, etc., existing in the bearing ring and steel ball run path are determined at step S18.

In a case where it is not necessary to set a value of the axial load to be a predetermined value, the pressure force of the outer ring press device 84 is controlled and the contact angle α is set to be a predetermined value. That is, first the bearing is made to be in a fitting state by the booster 86, and next the contact angle is detected if it becomes αA while increasing the pressure force of the outer ring press device 84. Both operations can be applied if appropriate.

Thus, the vibration measurement system 51 of the embodiment can evaluate vibration of the ball bearing unit under fit conditions matching the actual use state.

In the second embodiment, the state amount indicating the fit state of the rolling bearing is the rotation frequency of the inner ring and the revolution frequency of the ball and the contact angle calculated from the frequencies, and a predetermined value of the bearing clearance amount in the fit state is a unique clearance amount corresponding the case where the contact angle under predetermined axial pressure is a predetermined value.

In the embodiments, for example, an AE sensor, a piezoelectric device, an optical displacement meter, a speedmeter, an accelerometer, or the like can be used as the vibration detection means. A plurality of devices may be attached. They may be mounted at symmetrical positions of the outer ring and a noise signal common other than vibration may be subtracted for raising detection precision. The vibration detection means may be attached to the side of the bearing ring to detect axial vibration. Further, the hydraulic system is used to shrink the outer ring or expand the inner ring in the embodiments, but a collet chuck may be used in place of the hydraulic system.

Although cylindrical roller bearings are measured in the first embodiment, bearings of any other types may be measured if they are rolling bearings having no contact angle; for example, needle bearings with no inner ring can also be measured. Further, the deformation means is disposed in the housing in the first embodiment, but means for expanding the outer diameter of the arbor as in the second embodiment may be provided, for example. Although the inner ring is driven, with the inner ring fixed, the outer ring may be rotated for measuring vibration of the inner ring.

Although angular ball bearings are measured in the second embodiment, bearings of any other types may be measured if they are bearings having a contact angle; for example, the vibration measurement system is also applicable to tapered roller bearings, etc., in addition to ball bearings such as deep groove ball bearings. With the outer ring fitted into the housing, the deformation means may be disposed in the housing. In addition, changes similar to those in the first embodiment can be made.

Further, the state amount indicating the fit state and its detection means are not limited to those of the embodiments; they need only to be able to uniquely derive bearing clearance from the state amount. For example, in the first embodiment, the torque may be detected by another method, such as use of a strain gage.

That is, if it has deformation control means capable of controlling so as to uniformly deform the housing or mounting shaft radially so that the bearing clearance of the rolling bearing to be measured with the bearing fitted into the vibration measurement system becomes a predetermined value, it does not depart from the scope of the invention.

The vibration measurement system of a rolling bearing of the invention gives elastic deformation to the bearing ring radially without putting the bearing ring out of shape and adjusts the bearing clearance of the rolling bearing to a predetermined distance. In this state, it drives the rolling bearing by the drive means and detects vibration of the rolling bearing by the vibration detection means, so that it can accurately measure vibration of the rolling bearing.

That is, with bearings having no contact angle, such as cylindrical roller bearings, a load zone can be formed over the full periphery of the bearing ring, and all rolling elements can be in reliable contact with the bearing ring with no clearance. As a result, shock caused by so-called roller drop phenomenon does not occur, and defects such as flaws or foreign material within the rolling surface between the tracks of the outer and inner rings where the rolling elements roll can be detected accurately.

Also, contact between the rolling elements and the bearing ring changes from local contact to full peripheral contact, whereby a defect on the contact face between the bearing ring and the rolling elements can be reliably detected, and evaluation over the full periphery of a fixed ring is enabled by one set. Therefore, the measurement time can be shortened and the control configuration can be simplified as compared with the case where the fixed ring is rotated for moving the load zone and measurement is repeated.

With bearings having a contact angle such as ball bearings, the contact angle of the bearing at the measurement time can be matched with the contact angle in the fit state of an actually used close fit, etc. Thus, vibration evaluation of a bearing unit matching the actual use state can be executed.

What is claimed is:

1. A vibration measurement system for measuring a rolling bearing comprising: means for holding by fitting at least one of an inner ring and an outer ring of a rolling bearing to be measured having at least one bearing ring and a plurality of rolling elements; means for driving at least one of the inner ring and the outer ring of said rolling bearing fitted into said holding means; and means for detecting vibration of said rolling bearing, wherein the improvement comprises:

means for elastically deforming uniformly radially said holding means into which said rolling bearing is fitted whereby urging one of the inner ring and the outer ring of said rolling bearing radially toward said rolling elements;

clearance detection means for detecting a bearing clearance of the rolling bearing in a fit state between said rolling bearing and said holding means; and deformation control means for enabling the elastical deformation to be applied to said deformation means until an amount of the bearing clearance detected by said clearance detection means reaches a predetermined value.

2. The vibration measurement system according to claim 1, wherein said elastically deforming means comprises one of means for deforming said holding means radially inwardly so that the outer ring of the bearing shrinkages radially inwardly and means for expanding said holding means radially outwardly so that the inner ring of the bearing expands radially outwardly.

3. The vibration measurement system according to claim 1, wherein said clearance detection means comprises one of a torque detection means in a case where the rolling bearing is a bearing having no contact angle and a vibration detection means, in a case where the rolling bearing is a bearing having a contact angle, for calculating both a revolution frequency of the rolling elements driven by said driving means and a rotational frequency of a track of the bearing.

4. The vibration measurement system according to claim 1, wherein said deformation control means comprises an outer ring press device for applying an axial pressure to the bearing having a contact angle until the bearing clearance becomes a predetermined value.

* * * * *